US00PP18908P2

(12) United States Plant Patent
Yomo et al.

(10) Patent No.: US PP18,908 P2
(45) Date of Patent: Jun. 10, 2008

(54) ***SALVIA* PLANT NAMED 'SUNSARUSAMO'**

(50) Latin Name: *Salvia jamensis*
Varietal Denomination: Sunsarusamo

(75) Inventors: Yasunori Yomo, Kanagawa (JP); Takuro Ishihara, Tokyo (JP)

(73) Assignee: Syngenta Seeds B.V., Enkhuizen (NL)

( * ) Notice: Subject to any disclaimer, the term of this patent is extended or adjusted under 35 U.S.C. 154(b) by 31 days.

(21) Appl. No.: 11/698,654

(22) Filed: Jan. 26, 2007

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Matthew Edwards

(57) ABSTRACT

A new and distinct cultivar of *Salvia* plant named 'Sunsarusamo' characterized by its upright and relatively compact plant habit, freely basal branching habit, dense and bushy plant form, freely flowering habit, salmon colored flowers, and tolerance to high and lower temperatures.

1 Drawing Sheet

Latin name of the genus and species of the plant claimed: *Salvia jamensis*.
Varietal denomination: 'Sunsarusamo'.

BACKGROUND OF THE NEW PLANT

The present invention relates to a new and distinct cultivar of *Salvia* plant, botanically known as *Salvia jamensis,* and hereinafter referred to by the name 'Sunsarusamo.'

The new *Salvia* is a product of a planned breeding program conducted by the inventors in Higashiomi-shi, Shiga, Japan. The new cultivar 'Sunsarusamo' is compact with bushy growth habit and numerous flowers with attractive coloration.

The new *Salvia* originated from a self-pollination made by the inventors in April, 1998 of a proprietary *Salvia* selection identified as code number '97S34-2,' not patented. The new *Salvia* was discovered and selected by the inventors as a single flowering plant within the progeny of the stated cross-pollination grown in a controlled environment in Higashiomi-shi, Shiga, Japan.

Asexual reproduction of the new cultivar by cuttings and divisions taken at Higashiomi-shi, Shiga, Japan, since September, 2000, has shown that the unique features of this new *Salvia* are stable and reproduced true to type in successive generations.

BRIEF DESCRIPTION OF THE DRAWING

The accompanying colored photograph illustrate the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Salvia*.

BRIEF DESCRIPTION OF THE NEW CULTIVAR

Plants of the cultivar 'Sunsarusamo' have not been observed under all possible environmental conditions. The phenotype may vary somewhat with variations in environment such as temperature and light intensity without, however, any variance in genotype.

The following traits have been repeatedly observed and are determined to be the unique characteristics of 'Sunsarusamo'. These characteristics in combination distinguish 'Sunsarusamo' as a new and distinct *Salvia* cultivar:

1. Upright and relatively compact plant habit.
2. Freely basal branching, dense, and bushy plant form.
3. Freely flowering habit.
4. Salmon colored flowers.
5. Tolerant to high and lower temperatures.

DIFFERENCES BETWEEN 'SUNSARUSAMO,' ITS PATENTS AND THE MOST RESEMBLING VARIETIES

Plants of the new *Salvia* differ from plants of the parents primarily in flower color as plants of the female parent selection have red purple colored flowers.

Plants of the new *Salvia* differ from plants of the *Salvia* cultivars 'Sunsarupin,' U.S. Plant Pat. No. 15,215, and 'Sunsaruoro,' U.S. Plant Pat. No. 15,141, primarily in flower color.

Plants of the new *Salvia* can be compared to plants of the *Salvia* cultivar 'Navajo Salmon Red,' not patented. In side-by-side comparisons conducted in Enkhuizen, Holland, plants of the new *Salvia* differed from plants of the cultivar 'Navajo Salmon Red' in the following characteristics:

1. Plants of the new *Salvia* were more compact than plants of the cultivar 'Navajo Salmon Red.'
2. Plants of the new *Salvia* and the cultivar 'Navajo Salmon Red' differed in flower color as plants of the cultivar 'Navajo Salmon Red' had deep salmon red colored flowers.
3. Plants of the new *Salvia* and the cultivar 'Navajo Salmon Red' differed in sepal color as plants of the cultivar 'Navajo Salmon Red' had purple sepals and the new *Salvia* had green sepals.
4. Plants of the new *Salvia* were tolerant to lower temperatures than plants of the cultivar 'Navajo Salmon Red.'.

DETAILED BOTANICAL DESCRIPTION

Plants shown in the aforementioned photographs and used in the following description were grown under conditions which closely approximate commercial production conditions in the spring time in Holland. During the production of the plants, day temperatures were about 25 degrees C. and night temperatures were about 20 degrees C. The description was made on 37 week old plants that were grown in the filed in Enkhuizen, Holland.

Propagation Type : By cuttings.
Time to initiate roots : Summer: About 7 days at 25 degrees C. Winter: About 10 days at 20 degrees C.
Time to produce a rooted:
Young plant : Summer: About 30 days at 20–30 degrees C. Winter: About 40 days at 15–20 degrees C.
Root description : Fine, fibrous, freely branching, and light brown in color.
Plant description:
*Form.*—Perennial. Mostly upright and relatively compact plant habit; narrow inverted triangle. Freely basal branching, dense and bushy plant habit, vigorous growth habit. Flowers arranged in verticillasters on spikes.
*Plant height.*—About 99 cm.
*Plant width.*—About 60 cm.
Flowering stem description (Peduncles):
*Length.*—About 70 cm.
*Diameter.*—About 4 mm.
*Internode length.*—About 2–3 cm.
*Strength.*—Strong.
*Texture.*—Smooth, glabrous.
*Color.*—N199B.
Foliage description:
*Arrangement.*—Opposite, simple.
*Length.*—About 2.5 cm.
*Width.*—About 1.5 cm.
*Shape.*—Ovate.
*Apex.*—Rounded.
*Base.*—Obtuse.
*Margin.*—Crenulate.
*Texture, upper and lower Surfaces.*—Rough, waxy, glabrous.
*Venation.*—Pinnate.
*Color.*—Developing and fully expanded foliage, upper surface: 137A. Developing and fully expanded foliage, lower surface: 137C.
Petiole:
*Length.*—About 1.0 cm.
*Diameter.*—About 0.7 mm.
*Texture, upper and lower surfaces.*—Smooth, glabrous.
*Color.*—138B.
Flower description:
*Flower arrangement and shape.*—Single bilabiate flowers in verticillasters on spikes; flowers face upright and outwardly. Freely flowering, about 44 flowers and flower buds per spike.
*Natural flowering season.*—Continuous from spring to late autumn in Holland.
*Flower longevity on the plant.*—Individual flowers last about two to five days on the plant. Flowers not persistent.
*Fragrance.*—Faintly fragrant; sweet.
Flower buds:
*Length.*—About 1.1 mm.
*Diameter.*—About 3 mm.
*Shape.*—Obovate.
*Color.*—12A.
Inflorescence size:
*Length.*—About 19–24 cm.
Flowers:
*Diameter.*—About 1.5 cm.
*Depth (height).*—About 2.5 cm.
Petals:
*Arrangement.*—Bilabiate; one upper lip and one lower lip with two lobes; lips fused at the base.
*Length.*—Upper petal: About 9 mm. Lower petal: About 1.4 mm.
*Width.*—Upper petal: About 3 mm. Lower petal: About 1.3 cm.
Shape:
*Upper petal.*—Linear; hooded.
*Lower petal.*—Cordate.
*Apex.*—Upper petal: Hooked. Lower petal: Two-lobed.
*Margin, upper and lower petals.*—Entire.
*Texture, upper and lower petals.*—Satiny, smooth.
*Color, upper and lower petals.*—When opening and fully opened, upper surface: 41B. When opening and fully opened, lower surface: 41D.
Sepals:
*Arrangement.*—Two sepals fused into a tube.
*Length.*—About 1.3 cm.
*Width.*—About 5 mm.
*Shape.*—Triangular.
*Apex.*—Acute.
*Margin.*—Entire.
*Color, upper and lower surfaces.*—138A with upper tip of tube is 139A.
Pedicels:
*Strength.*—Moderately strong.
*Length.*—About 5 mm.
*Diameter.*—About 1 mm.
*Aspect.*—About 40 degrees from vertical.
*Texture.*—Smooth, glabrous.
*Color.*—137C.
Reproductive organs:
*Stamens.*—Quantity per flower. Two.
*Anther shape.*—Ovate.
*Anther length.*—About 15 mm.
*Anther color.*—155C.
*Pollen amount.*—Moderate.
*Pollen color.*—15A.
*Pistils.*—Quantity per flower One.
*Pistil length.*—About 3.2 cm.
*Stigma shape.*—Two-parted.
*Stigma color.*—47D.
*Style length.*—About 3.0 cm.
*Style color.*—155D.
*Ovary color.*—3C.
Seed/fruit: Seed and fruit production has not been observed.
Disease/pest resistance: Plants of the new *Salvia* have not been noted to be resistant to pathogens and pests common to *Salvia*.
Temperature tolerance: Plants of the new *Salvia* have been observed to tolerate temperatures from −10 to 40 degrees C.

What is claimed is:

1. A new and distinct cultivar of *Salvia* plant named 'Sunsarusamo,' substantially as herein illustrated and described.

* * * * *

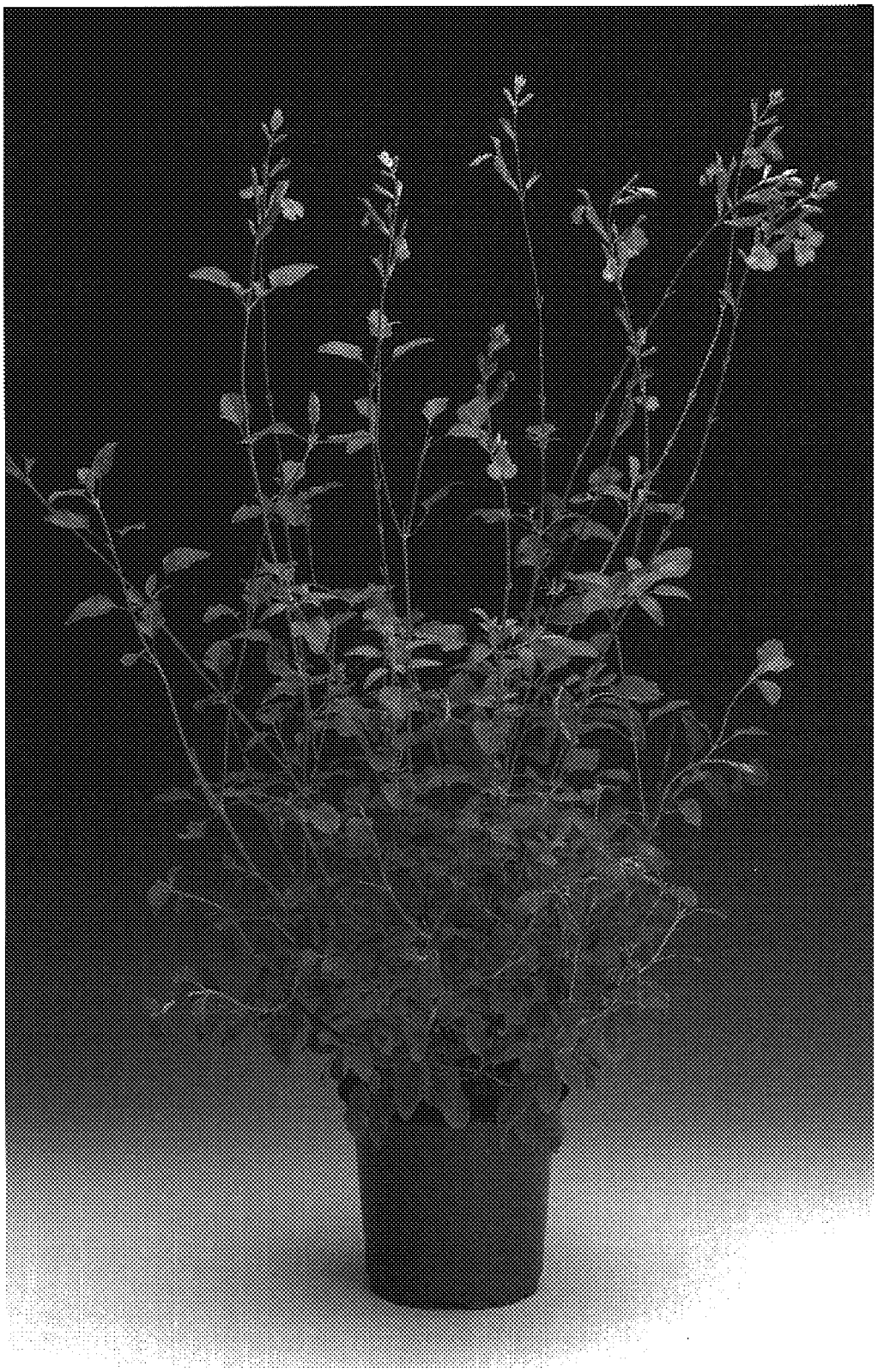

UNITED STATES PATENT AND TRADEMARK OFFICE

CERTIFICATE OF CORRECTION

PATENT NO. : PP 18,908 P2
APPLICATION NO. : 11/698654
DATED : June 10, 2008
INVENTOR(S) : Yomo et al.

It is certified that error appears in the above-identified patent and that said Letters Patent is hereby corrected as shown below:

At column 1, line 14, delete "PATENTS" and insert therefor --PARENTS--

At column 3, within the "DETAILED BOTANICAL DESCRIPTION" and following "grown in the", delete "filed" and insert therefor --field--

Signed and Sealed this

Twenty-ninth Day of July, 2008

JON W. DUDAS
*Director of the United States Patent and Trademark Office*